United States Patent [19]

Bohlin

[11] Patent Number: 4,552,012

[45] Date of Patent: Nov. 12, 1985

[54] RHEOMETER FOR ANALYZING THE ELASTIC AND/OR VISCOUS CHARACTERISTICS OF GELS AND LIQUID SYSTEMS

[76] Inventor: Leif R. Bohlin, Krankesjövägen 12, S-240 15 Södra Sandby, Sweden

[21] Appl. No.: 478,558

[22] PCT Filed: Jul. 19, 1982

[86] PCT No.: PCT/SE82/00246

§ 371 Date: Mar. 15, 1983

§ 102(e) Date: Mar. 15, 1983

[87] PCT Pub. No.: WO83/00387

PCT Pub. Date: Feb. 3, 1983

[30] Foreign Application Priority Data

Jul. 20, 1981 [SE] Sweden .............................. 8104453

[51] Int. Cl.⁴ ............................................ G01N 11/16
[52] U.S. Cl. ............................................ 73/59; 73/54
[58] Field of Search ...................... 73/54, 59, 32, 32 A

[56] References Cited

U.S. PATENT DOCUMENTS

| | | | |
|---|---|---|---|
| 1,651,596 | 12/1927 | Hall et al. ................................ | 73/59 |
| 3,903,732 | 9/1975 | Rork et al. ............................... | 73/54 |
| 4,117,716 | 10/1978 | Simon ...................................... | 73/54 |
| 4,166,381 | 9/1979 | Woo ......................................... | 73/54 |
| 4,341,111 | 3/1980 | Husar ....................................... | 73/59 |

FOREIGN PATENT DOCUMENTS

| 205235 | 12/1908 | Fed. Rep. of Germany .......... | 73/59 |
|---|---|---|---|
| 171191 | 4/1960 | Sweden .................................... | 73/59 |
| 830463 | 3/1960 | United Kingdom ..................... | 73/59 |
| 1175347 | 12/1969 | United Kingdom . | |

OTHER PUBLICATIONS

J. G. Woodward, Vibrating Plate, RCA, 2-1952.

*Primary Examiner*—Stewart J. Levy
*Assistant Examiner*—Hezron E. Williams
*Attorney, Agent, or Firm*—Charles R. Mattenson

[57] ABSTRACT

A rheometer for analyzing the elastic and/or viscous characteristics of gels and liquid systems, comprising a movable member (14), preferably in the form of a rockable disk which, on one side, is in contact with the gel or the liquid system and, on its opposite side, has a device (22) for rocking said disk, and means (25) for measuring the resistance of the gel or the liquid system to such rocking motion of the disk.

12 Claims, 3 Drawing Figures

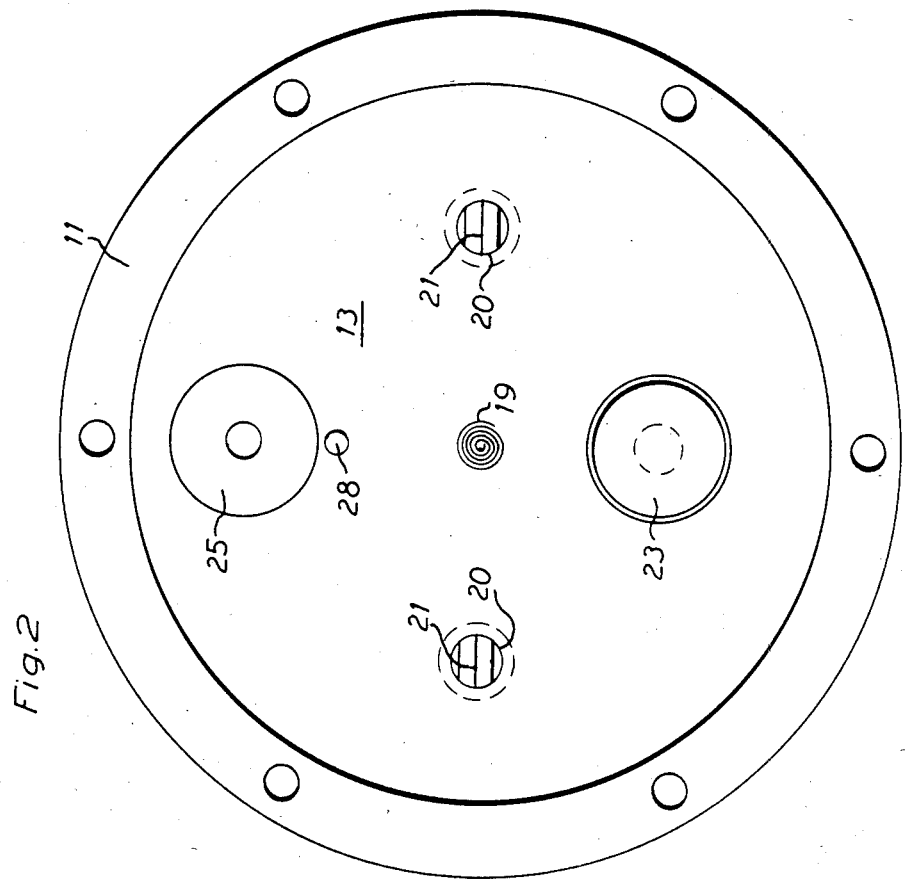
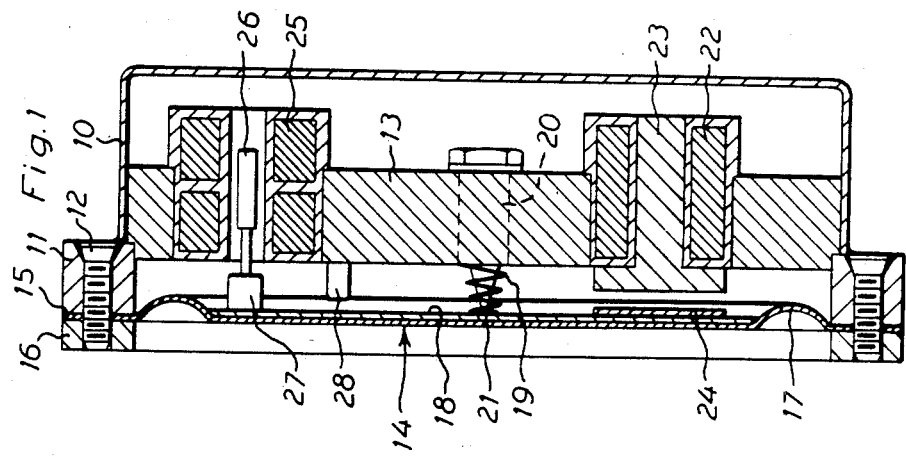

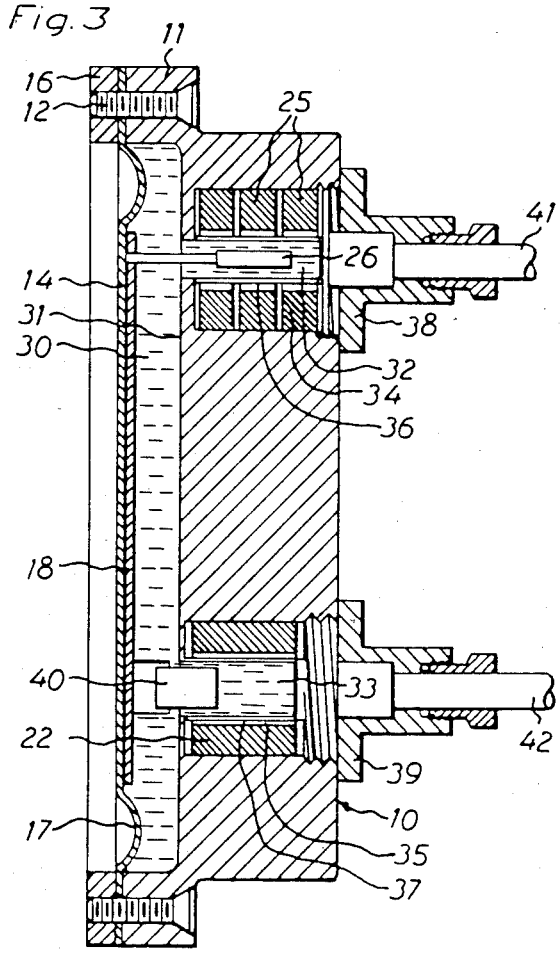

RHEOMETER FOR ANALYZING THE ELASTIC AND/OR VISCOUS CHARACTERISTICS OF GELS AND LIQUID SYSTEMS

BACKGROUND OF THE INVENTION

1. Field of the Invention

The present invention relates to a rheometer for analyzing the elastic and/or viscous characteristics of gels and liquid systems.

2. The Prior Art

It is frequently desired to be able continuously to check the elastic and/or viscous characteristics of a gel or liquid system, for example in the production of cheese where the coagulation of the curd must be interrupted at the correct time to ensure a satisfactory final result. At present, these coagulation checks are made by an expect, the cheese-maker, who at regular intervals takes samples of the curd and, by his expert knowledge, decides when coagulation is to be interrupted. It is obvious that such assessment requires a great deal of experience and that, nevertheless, errors may occur, for instance if the checks are not made continuously. In view hereof, there has been a long-felt demand in this particular field for some type of measuring and monitoring device which indicates when coagulation should be interrupted. Naturally, similar requirements exist in other technical fields, and the need for a simple and inexpensive device for determining the elastic and/or viscous characteristics of a gel or a liquid system is considerable.

SUMMARY OF THE INVENTION

According to the present invention, a device for the purpose here concerned comprises a movable member, a surface portion of which is in contact with the gel or the liquid system underneath the surface thereof, a device for displacing said member substantially perpendicular to said surface against the action of the gel or the liquid system, and means for measuring the resistance to such displacement.

BRIEF DESCRIPTION OF FIGURES

The invention will now be described in greater detail, reference being had to the accompanying drawings which illustrate an embodiment and in which FIG. 1 is a cross-section of a rheometer according to the invention;

FIG. 2 shows the interior of the rheometer; and

FIG. 3 is a cross-section of a modified embodiment.

DETAILED DESCRIPTION OF THE PREFERRED EMBODIMENT

According to FIG. 1 the rheometer of the present invention comprises a cup-shaped casing 10 having a flange 11 around its periphery adjacent the open end of the cup. The flange 11 has a number of equidistantly spaced apart apertures for accommodating screws 12, as will be described in greater detail in the following. A holder 13 in the form of a planar plate is so mounted in the cup 10, for instance by means of screws, that it extends in parallel with the bottom of the casing 10. The open end of the casing 10 is closed by means of a diaphragm 14, the peripheral portion 15 of which is clamped between the outwardly facing side of the flange 11 and a clamping ring 16 by means of the screws 12 engaging with threaded bores in the ring 16. The diaphragm which is made of, for example, textile-reinforced nitrile rubber, is movably connected with the open end of the casing 10 approximately in the manner of a loudspeaker cone, as shown at 17.

For reinforcing purposes, the diaphragm 14 is provided on its inner side with a plate 18 extending over the major part of the area of the diaphragm 14. The reinforcing plate 18 may be made of plastics or metal and is connected with the diaphragm in some suitable manner. As will appear from FIG. 2, a tension spring 19 is connected to the centre of the diaphragm 14 and the reinforcing plate 18, respectively. The opposite end of the spring is connected to the holder plate 13. On either side of the said centre point, there is mounted in the holder plate 13 a knife-edge arrangement 20 with its edge 21 facing the diaphragm and the plate 18. The knife edges 21 extend along the diameter of the diaphragm. The inner side of the reinforcing plate 18 of the diaphragm 14 is held in engagement with the knife edges 21 by the spring 19. By being suspended and supported in this manner, the diaphragm 14 is capable of rocking on the knife edges 21.

Beneath the above-mentioned centre, there is secured to the holder plate 13 a coil 22 having an armature 23 with a shank extending through the coil and a disk engaging with the coil end facing the diaphragm. Opposite the disk-shaped portion of the coil core, an iron plate 24 is attached to the reinforcing plate 18. By activation of the coil 22, the iron core of the coil can be made to attract the iron plate 24 on the plate 18 of the diaphragm 14, as a result of which the entire diaphragm will rock on the knife edges 21. FIG. 1 shows a stationary iron core 23 which, however, may be replaced by a movable core which, in that case, is connected with the reinforcing plate 18 for direct actuation of the diaphragm 14.

Disposed over the centre is a measuring device in the form of a differential coil 25 in which an activating member 26 is movable. The member 26 is connected with the plate 18 of the diaphragm 14 by means of an attachment 27. Upon rocking of the diaphragm 14, the member 26 will thus move back and forth within the coil 25, and by connecting said coil to a suitable measuring device it is possible, as will be more clearly apparent from the following description, to determine the resistance to which the diaphragm 14 is subjected by the rocking action of the arrangement 22, 23 and 24. The resistance of rocking may also be measured optically or in some other manner well known to one skilled in the art.

FIG. 3 illustrates another embodiment in which the casing 10 is a massive body having a circumferential flange 11. The massive body is provided, in one of its flat sides, with a recess 30 having a planar bottom surface 31 which is parallel to the said flat side. The bottom surface 31 has two bores 32, 33 which extend towards the other flat side of the body and are positioned at a predetermined diametrical distance from one another, approximately in the same manner as the previously described means 23 and 26. As will be seen, the bores do not extend right up to the other flat side of the casing, but terminate at a distance therefrom. Alternatively, they may extend right through said body and be sealed at their end opening into the other flat side. The other flat side of the body has two recesses 34 and 35 which are annular in cross-section and each surround coaxially one of the bores 32 and 33, but are separated therefrom by means of a thin wall 36 and 37, respectively. The recesses 34 and 35 terminate at some distance from the bottom surface 31 of the recess 30 and, at their opposite ends, are sealed towards the atmosphere by means of screw covers 38 and 39, respectively, which also serve as cable lead-ins.

The casing has on its front side a diaphragm 14 which is connected therewith in liquid-tight manner, as previously described with reference to FIG. 1. As in the embodiment previously described, there is attached to the rear side of the diaphragm a reinforcing plate 18 with which an activating member 26 is connected which projects into the bore 32 in order to activate a differential coil 25 disposed within the recess 34 and connected to external measuring means by a cable 41 which is passed through the cover 38. Instead of the iron plate 24 in the embodiment previously described, the reinforcing plate here carries a permanent magnet 40 which can be actuated by a coil 22 provided in the recess 35 and connected to an external current source via a cable 42 extending through the cover 39.

The recess 30 and the bores 32, 33 therein are filled with a suitable liquid, such as distilled water, which thus replaces the knife-edge arrangement of the embodiment previously described.

The embodiments described above are used in the following manner for checking the elastic and/or viscous characteristics of a gel or a liquid system. Preferably, the device is built into the wall of the vessel containing the gel or the liquid system, such that the diaphragm 14 will be on a level with the inner surface of the container, which is advantageous because the rheometer thus will not obstruct the stiring means frequently utilized in containers of this type. After the gel or the liquid system to be monitored has been filled into the container so that it covers the outer side of the diaphragm 14, the rheometer can be started by applying a suitable voltage to the coil 22. This voltage preferably is obtained from a power amplifier connected to a low-frequency generator. The frequency is set at a suitable value which, for the monitoring of curd, may be 0.5 Hz. As a result, the diaphragm 14 will be rocked at this frequency, and the liquid contacting the outer side of the diaphragm will exert a characteristic resistance to the rocking movement in response to the elasticity or viscosity of the liquid. This resistance is measured by means of the coil 25 with the member 26 movable therein, or by means of some other suitable measuring device, in a simple and reliable manner. After processing, the measuring result can be applied to, for example, a recorder so that the coagulation process can be supervised continuously. It is also possible to connect an alarm device or means for instantaneously interrupting the coagulation as soon as a predetermined coagulation value has been attained.

As a rule, the rheometer is equipped with means adapted to prevent excessive inward movement within the casing, especially if the diaphragm is thin and sensitive. Such inward movement may be due to a high static liquid pressure on the diaphragm, or to pressure transients. In the embodiment as first described above, this means may consist of limiting means 28 which are secured to the holder or, in their simplest form, are constituted by the holder itself which in that case is positioned closer to the diaphragm than is shown in FIG. 1, or designed in some other manner suitable for the purpose intended. In the embodiment according to FIG. 3, no additional limiting means are required since the liquid within the recess 30 has itself this limiting function.

Naturally, it is also possible to dispose the casing 10 with the flange 11, the clamping ring 16 and the diaphragm 14 in a liquid-tight manner in the embodiment according to FIG. 1, and to fill the casing with a suitable liquid, such as oil.

It will be obvious to those skilled in the art that the rheometer may be modified in many different ways. The surface contacting the gel or the liquid system need not necessarily be a diaphragm, but may consist, for example, of the end face of a piston which, in some suitable manner, is movable into and out of a cylinder. Furthermore, the measuring surface need not be rockable, but may instead be linearly displaceable back and forth. Furthermore, the measuring device need not be in the form of a seperate unit of the rheometer since it is also possible to determine the resistance of the liquid by measuring the current consumption upon displacement of the means disposed within the gel or the liquid system. The displacement or rocking frequency is varied on the basis of the characteristics of the monitored liquid, but it is pointed out that, with low frequencies, such as 0.5 Hz, the elastic characteristics of the liquid are measured, whereas, if both the elastic and the viscous characteristics are to be checked, the frequency must normally be increased to 10-20 Hz.

I claim:
1. A rheometer for analyzing the elastic and viscous characteristics of a medium, comprising:
   a casing supporting a movable member, a region of which is in contact with a surface of the medium, said movable member is liquid-impermeable, is affixed across an opening of said casing and is movable against the action of a liquid body within said casing;
   a device affixed to said casing for displacing said region of said movable member substantially perpendicular to said surface non-destructively against the action of said medium; and
   electrical means affixed to an interior surface of said casing for measuring the elastic and viscous characteristics by electrically measuring the resistance to such displacement.

2. A rheometer for analyzing the elastic and viscous characteristics of a medium, comprising:
   a casing supporting a movable member, a region of which is in contact with a surface of the medium, said movable member covers an opening of a cup-shaped casing in which there is provided a holder which carries a support in the form of at least one knife-edge member secured in said holder and having a knife edge directed towards an inner side of said member;
   a tension spring affixed to an inner surface of said casing for maintaining said inner side of said movable member in rockable engagement with said knife edge;
   means for limiting the inward movement of said movable member;
   a device affixed to said casing for displacing said region of said movable member substantially perpendicular to said surface non-destructively against the action of the medium; and
   electrical means affixed to an interior surface of said casing for measuring the elastic and viscous characteristics by electrically measuring the resistance to such displacement.

3. A rheometer as claimed in claim 1, wherein said device for displacing said region of said member comprises a coil affixed to said casing and a cooperative member, affixed to said movable member, for displacing said region of said movable member in response to electrical current of a selected frequency applied to said coil.

4. A rheometer as claimed in claim 1, wherein said means for measuring the elastic and viscous characteristics of the medium comprises a coil affixed to an interior surface of said casing and an activating member secured to said movable member.

5. A rheometer as claimed in claim 1, wherein said movable member is a disk-shaped member which comprises a diaphragm which is secured to said casing approximately in the manner of a loudspeaker cone and, on a surface facing said casing, has a reinforcing member of a selected material affixed thereto.

6. An apparatus for non-destructivity measuring the viscous characteristic of a selected medium comprising:
 a housing with an opening formed therein;
 a diaphragm covering said opening forming an enclosed space with a peripheral region thereof affixed to said housing such that a region of said diaphragm adjacent said space is deflectable a limited distance;
 means for deflecting including a deflecting coil, affixed to said housing within said space, said deflecting means being responsive to an electric signal of a selected frequency applied thereto for deflecting said region of said diaphragm substantially perpendicular to a surface of the medium whose viscous characteristic is to be measured; and
 means for sensing including a sensing coil, affixed to said housing in said space, for producing an electric signal responsive to the amount of movement of said diaphragm with respect to the surface of the medium.

7. A measuring apparatus in accordance with claim 6 wherein said deflecting and said sensing coils are spaced apart and positioned along a selected diameter of said diaphragm.

8. A measuring apparatus in accordance with claim 7 including a rigid member affixed to an interior surface of said diaphragm and means for limiting movement of said member positioned adjacent said member at least along a second diameter of said diaphragm essentially perpendicular to said first diameter.

9. A measuring apparatus in accordance with claim 8 wherein said means for limiting includes:
 a selected liquid disposed in at least a part of said space adjacent said rigid member.

10. A measuring apparatus in accordance with claim 8 wherein said means for limiting includes:
 at least a first rocking member, affixed to said housing within said space, spaced apart from said coils with a rocking surface located adjacent said rigid member for permitting rocking motion thereof in response to the electrical current of the selected frequency being applied to said deflecting coil.

11. A measuring apparatus in accordance with claim 10 wherein said means for limiting further includes:
 a tension spring affixed to said housing within said space for holding said rigid member against said rocking surface.

12. A measuring apparatus in accordance with claim 11 wherein said means for limiting further includes:
 a second rocking member affixed to said housing in said space, said first and second rocking members being spaced apart from one another along said second diameter with said tension spring therebetween.

* * * * *